US010589182B2

(12) United States Patent
Helmick et al.

(10) Patent No.: US 10,589,182 B2
(45) Date of Patent: Mar. 17, 2020

(54) WATER ATTRACTION DISPATCH SYSTEM

(71) Applicant: Universal City Studios LLC, Universal City, CA (US)

(72) Inventors: David Helmick, Winter Park, FL (US); Elliot Taylor, Winter Springs, FL (US); Justin Michael Schwartz, Orlando, FL (US)

(73) Assignee: Universal City Studios LLC, Universal City, CA (US)

( * ) Notice: Subject to any disclaimer, the term of this patent is extended or adjusted under 35 U.S.C. 154(b) by 0 days.

(21) Appl. No.: 16/107,325

(22) Filed: Aug. 21, 2018

(65) Prior Publication Data

US 2019/0358550 A1 Nov. 28, 2019

Related U.S. Application Data

(60) Provisional application No. 62/676,018, filed on May 24, 2018.

(51) Int. Cl.
| | |
|---|---|
| *A63G 31/00* | (2006.01) |
| *G01N 31/22* | (2006.01) |
| *A63G 21/18* | (2006.01) |
| *G07C 9/00* | (2020.01) |
| *G01F 23/00* | (2006.01) |

(52) U.S. Cl.
CPC ........... *A63G 31/007* (2013.01); *A63G 21/18* (2013.01); *G01F 23/0069* (2013.01); *G01N 31/221* (2013.01); *G07C 9/00896* (2013.01)

(58) Field of Classification Search
CPC .. A63G 31/007; A63G 21/18; G01F 23/0069; G01N 31/221; G07C 9/00896

USPC ......................................................... 472/117
See application file for complete search history.

(56) References Cited

U.S. PATENT DOCUMENTS

| 4,805,897 A | * | 2/1989 | Dubeta | A63G 21/18 |
| | | | | 104/70 |
| 6,758,231 B1 | | 7/2004 | Lochtefeld et al. | |
| 7,740,542 B2 | * | 6/2010 | Henry | A63G 21/18 |
| | | | | 472/128 |
| 8,079,916 B2 | | 12/2011 | Henry | |
| 8,152,648 B2 | * | 4/2012 | Shipley | A63G 31/007 |
| | | | | 4/488 |
| 2002/0193169 A1 | * | 12/2002 | Dubeta | A63G 21/02 |
| | | | | 472/117 |
| 2005/0274420 A1 | | 12/2005 | Lochtefeld et al. | |
| 2007/0049388 A1 | | 3/2007 | Henry et al. | |
| 2007/0087850 A1 | | 4/2007 | Henry et al. | |

(Continued)

OTHER PUBLICATIONS

PCT/US2019/032044 International Search Report and Written Opinion dated Aug. 16, 2019.

*Primary Examiner* — Michael D Dennis
(74) *Attorney, Agent, or Firm* — Fletcher Yoder, P.C.

(57) ABSTRACT

A water attraction dispatch system includes a water attraction having a plurality of sensors and a dispatch controller. The dispatch controller is configured to receive attraction condition data from the plurality of sensors of the water attraction and determine a dispatch status of the water attraction based on the attraction condition data. The dispatch status may be a permit dispatch status or a deny dispatch status. The dispatch controller is configured to transmit a signal indicative of the dispatch status to a controller of the water attraction.

15 Claims, 6 Drawing Sheets

(56) References Cited

U.S. PATENT DOCUMENTS

| | | | |
|---|---|---|---|
| 2007/0257806 A1* | 11/2007 | Madden | G01N 33/18 340/603 |
| 2011/0028227 A1* | 2/2011 | Dubois | A63G 21/18 472/117 |
| 2018/0129984 A1 | 5/2018 | Polk et al. | |

* cited by examiner

WATER ATTRACTION DISPATCH SYSTEM

CROSS-REFERENCE TO RELATED APPLICATIONS

The present application claims the benefit of U.S. Provisional Application No. 62/676,018, entitled "WATER ATTRACTION DISPATCH SYSTEM," and filed May 24, 2018, the disclosure of which is incorporated herein by reference for all purposes.

BACKGROUND

The present disclosure relates generally to the field of amusement parks. Specifically, embodiments of the present disclosure relate to techniques to manage amusement park operations, including patron dispatch intervals for water park attractions.

Water amusement parks have substantially grown in popularity in recent years. To address this increasing demand, water amusement parks have been expanding by adding new types of attractions and increasing the throughput of existing attractions. The addition of attractions, such as water slide rides, generally provides a water amusement park with additional capacity to handle a larger number of guests. However, the higher guest throughput results in additional maintenance and park monitoring complexities. For example, water composition is a water condition that may vary as the number of guests in the water increases and that is monitored on a periodic basis. Assigning operators to monitor and/or resolve water condition tasks may result in inefficient park operations, as the operator may also be tasked with operating a guest queue for a ride.

Thus, while the additional attractions allow for additional guests and higher throughput, the complexity of monitoring the various water conditions may also increase. Such complex monitoring may further demand additional operator assistance to validate that water conditions are acceptable, resulting in potential delays for guest dispatch in the attraction.

SUMMARY

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

Provided herein is a water attraction dispatch system. The water attraction dispatch system includes a water attraction; a plurality of sensors of the water attraction; and a dispatch controller comprising a processor and a memory, wherein the memory stores instructions executable by the processor. The instructions are configured to cause the dispatch controller to receive attraction condition data from the plurality of sensors of the water attraction; determine a dispatch status of the water attraction based on the attraction condition data, wherein the dispatch status comprises a permit dispatch status or a deny dispatch status; and transmit a signal indicative of the dispatch status to a controller of the water attraction.

Also provided herein is a method that includes the steps of generating attraction condition data using a plurality of sensors of a water attraction; transmitting the attraction condition data to a dispatch controller; determining that an attraction condition of the water attraction is outside of a pre-determined tolerance based on the attraction condition data; transmitting a deny dispatch signal to an attraction controller; and maintaining a status associated with a deny dispatch signal at a dispatch location of the water attraction or maintaining a gate at the dispatch location in a closed position based on the deny dispatch signal.

Also provided herein is a water attraction that includes a plurality of sensors distributed about the water attraction, the plurality of sensors configured to measure one or more attraction conditions to generate attraction condition data; an attraction controller configured to receive dispatch control instructions based on the attraction condition data and to alter a dispatch interval based on the dispatch control instructions; and at least one dispatch indictor configured to display an indication of a dispatch status indicative of the dispatch control instructions.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
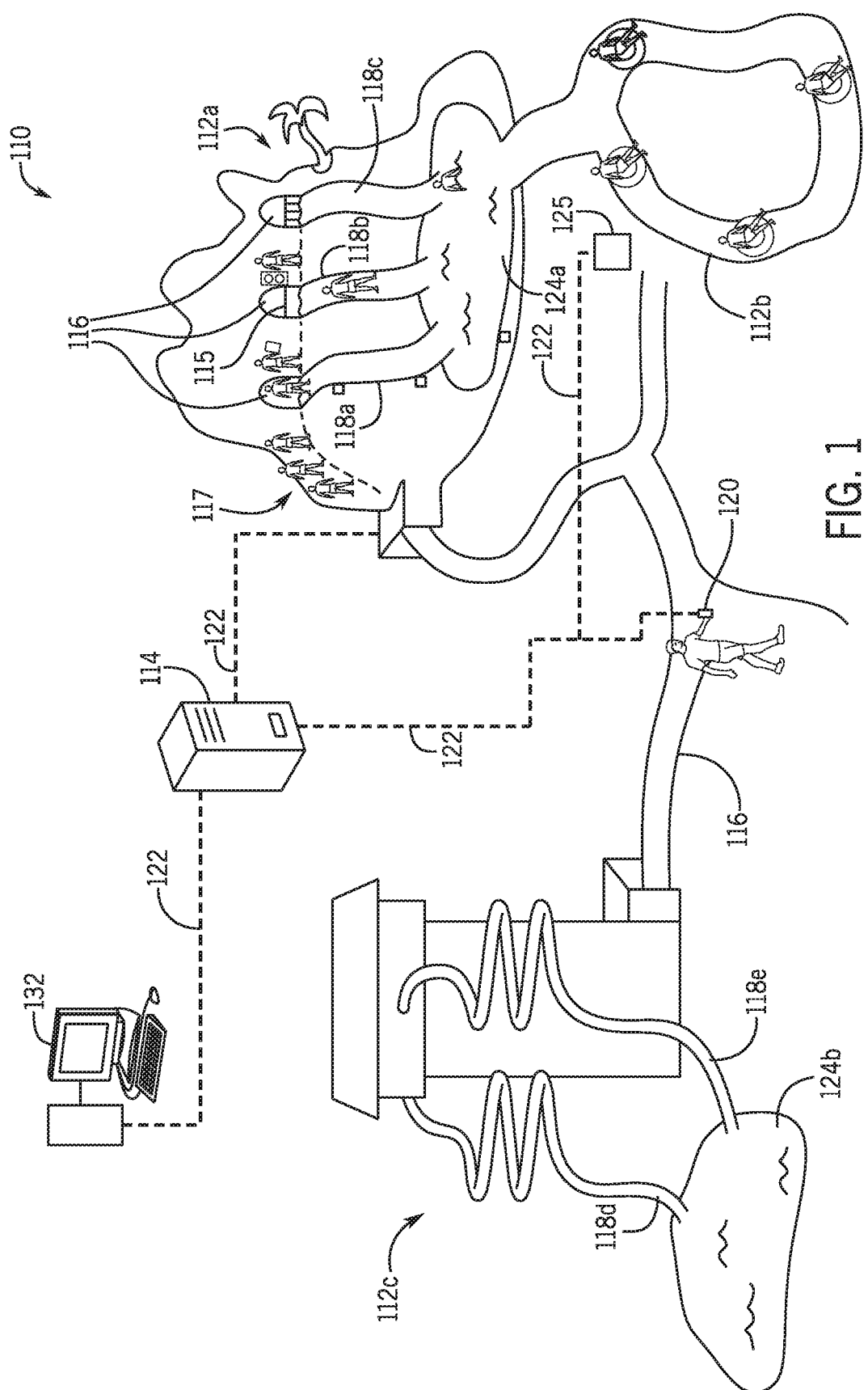
FIG. 1 is a schematic view of a theme park including a water attraction utilizing a water attraction dispatch system in accordance with present techniques.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment"

or "an embodiment" of the present disclosure are not intended to be interpreted as excluding the existence of additional embodiments that also incorporate the recited features.

Conditions of a water attraction (e.g., a water slide) may be prone to changes as the number of guests using the water attraction increases, as the weather changes, and due to conditions of the water pumping and/or supply systems for the various rides. Further, a change in attraction conditions may impact multiple attractions that share a water supply. In another example, certain changes may also impact parts of a single attraction while not impacting other parts. For example, a water slide with multiple slides may have different conditions on each slide depending on a condition of the water jets supplying each individual slide.

Additionally, guest throughput for an attraction may be impacted based on the attraction condition information. Guests may be dispatched to the attraction (e.g., authorized to enter the attraction) based on the various attraction conditions being within a given tolerance for each individual attraction condition that is monitored. That is, so long as the attraction has acceptable attraction conditions, the attraction operator is authorized to dispatch guests (e.g., send guests at regular intervals onto a water slide). However, providing information related to the acceptable attraction conditions to the attraction operator may be complex. Some attraction condition monitoring architectures may involve having the attraction operator assess the collected test and condition data to verify that each of the attraction conditions are within a given tolerance (e.g., sanitation tolerance for water composition, water pH, water temperature, water level, etc.). However, relying on the attraction operator to perform the attraction condition verification task may distract from the ability to smoothly manage guest throughput and dispatching. Further, the architecture may include multiple operators checking or resolving issues, providing data to the control system, and reviewing of the data by monitoring personnel, which may result in unreasonable delay between guest dispatches. Additionally, there may be inconsistent attraction condition readings by the various operators, which may result in additional delay. Still further, the individual attraction operators may have different efficiencies in distributing and loading guests into respective water slides. Thus, the overall water attraction monitoring and operating architecture may be inefficient and inaccurate, which may result in unnecessary wait time for guest dispatch, which in turn may result in longer queues and decreased guest enjoyment of the water amusement park.

It should be noted that although examples provided herein may be presented generally in a water amusement park and water attraction context, such as using the present techniques to facilitate attraction condition monitoring and guest dispatching by monitoring various attraction condition factors of a water attraction to efficiently dispatch guests, the techniques in this disclosure may be applied to other attractions of an amusement park (e.g., non-water attractions) and non-water related conditions and/or contexts. The non-water attraction and non-water related conditions may include general theme park rides (e.g., roller coaster) and the conditions checked prior to dispatching a guest may be related to various features of a ride or attraction.

With the foregoing in mind, FIG. 1 is a schematic representation of a water theme park 110 with at least one water attraction 112 that permits dispatch of guests in the water attraction 112a based on a water attraction dispatch controller 114. Certain water attractions 112 may feature a plurality of water slides 118. For example, in the depicted embodiment, a water attraction 112 may include multiple water slides (e.g., water slides 118a, 118b, and 118c) that may be accessed via a single dispatching queue 117 or dispatching group (e.g., a group of guests not in queue located in the dispatch location 116), which may permit access to a dispatch location 116 for the guests. In this manner, the guests may assume a position in the queue 117 for the water attraction 112 to enter the dispatch location 116. The dispatch location 116 may also include a guest sensor at the dispatch location 116 to track guest entry into the attraction 112. In one example, the dispatch location 116 may include an entry platform (in some embodiments, a trap door 115) that may indicate the presence of a guest via a senor (e.g., optical, RFID, or weight sensor) as discussed in further detail in FIG. 2. The presence of a guest at the dispatch location 116, e.g., on the trap door 115, may be used as part of the attraction condition assessment, e.g., to determine dispatch readiness, and/or to determine queue wait times. That is, the sensor provides a feedback signal to the system. Once in the dispatch location 116, the guests may be distributed between the separate water slides 118 by attraction operators to experience the water attraction 112. Accordingly, in the depicted embodiment, the water attraction 112 is capable of accommodating multiple guests (e.g., two, three, or more) at a time. Although multiple water slides 118 are shown, an individual water attraction 112 may include any suitable number of water slides 118 to accommodate any suitable number of guests per slide including, but not limited to, single water slides for an attraction. As shown, the guests may enter their assigned water slide 118 at different dispatch rates depending on a dispatch interval for the single water slide 118 and/or overall interval for the shared water pool 124a.

For example, attraction conditions may be satisfied (e.g., within tolerance) for water slides 118a and 118b, while one or more attraction conditions, such as water injection for water slide 118c, may not be satisfied. When the overall attraction conditions for water slide 118c are not be within tolerance, the water attraction dispatch controller 114 may generate a signal to deny permission to dispatch the guest in queue for either only the slide 118c or the overall water attraction 112a, depending on a stored instruction for the water attraction dispatch system. Accordingly, monitoring multiple attraction conditions and determining a guest dispatch for a water attraction 112 may be complex and may involve considering various water related and attraction related conditions.

In one embodiment, guest dispatch intervals provided by the water attraction dispatch controller 114 may be synced to a system controlling a virtual queue and in communication with a guest-associated device 120 (e.g., smart phone, guest wrist band). The guest-associated device 120 may be used to indicate waiting times for park attractions, such as a multi-slide or single-slide water attraction 112 or other attraction types (e.g., a lazy river attraction 112b) or positions in a virtual queue, such that one or more of the water attractions 112 do not have a physical queue 117 or such that any physical queue 117 is of shorter length.

The water attraction dispatch controller 114 may provide information that results in an increase or decrease in the dispatch interval for the water attraction 112 depending on an attraction condition change as monitored and determined by the water attraction dispatch controller 114. For example, in one embodiment, if the water attraction dispatch controller 114 determines an attraction condition (or at least one attraction condition) is out of tolerance for a particular water attraction 112, guest dispatch may cease until the situation is resolved (i.e., the status of the water attraction is maintained as or changed to a deny dispatch status, and the guest dispatch interval is increased or halted such that no new dispatches are permitted). As a result, the overall wait time for the water attraction 112 may also increase. In other embodiments, as noted herein, the result of an attraction condition outside of pre-set tolerances may result on other outcomes, such as partial or complete closure of the water attraction 112, which may also influence wait times. For example, if one slide 118 of a multi-slide water attraction 112 is closed, then the guests may be diverted to the remaining open slides 118.

The dispatch interval for the individual guest for the water attraction 112 may be based at least on one or more factors including the number of water slide(s) available for use, the presence of attraction condition(s) out of tolerance, the average time to resolve the attraction condition(s) out of tolerance, the time interval from when a notification of the attraction condition(s) out of tolerance to the time an operator is assigned to resolve attraction condition(s) that are out of tolerance, the water attraction water slide(s) dispatch interval data, and/or historical guest throughput at the water attraction 112. Accordingly, the guest-associated device 120 may be updated via a dispatch interval notification 122 to indicate the change in wait time for the associated water attraction 112.

In some embodiments, the water attraction dispatch controller 114 may be centralized and contain multiple notification 122 systems and/or connections (e.g., wired and/or wireless connections) to other systems in the park. In one example, a task notification may be communicated to and from the water attraction dispatch controller 114 to indicate an attraction condition out of tolerance to assign as a task for an operator. The attraction condition notification may be provided via signals transmitted from the water attraction 112 based on sensors located on various parts of the water attraction 112 as discussed herein. The sensors may be used by the water dispatch controller 114 to monitor attraction conditions and detect any changes in the attraction conditions. The water attraction dispatch controller 114 may use the sensor data to monitor and determine that attraction conditions remain within a pre-determined tolerance.

In the depicted embodiment, the water attraction dispatch controller 114 may be centralized and connected to other parts of the park. When the water attraction dispatch controller 114 determines a change in attraction conditions based on signals communicated from sensors on the water attraction 112, the water attraction dispatch controller 114 may send an alert of the changes to a monitoring system 132. The monitoring system 132 may be a user or virtual machine that sends real time attraction conditions and/or changes, and task notifications to assign an operator to resolve the attraction condition change that may be above or below the predetermined threshold, or out of tolerance. Additionally, the monitoring system 132 may be a secondary checking system that not only monitors alerts and/or notifications received by the water attraction dispatch controller 114, but may also control or reconfigure the water attraction dispatch controller 114. In this manner, the monitoring system 132 may reset attraction condition tolerances or override automated actions as a result of changes detected by the water attraction dispatch controller 114. For example, the water attraction dispatch controller 114 may automatically take action to permit or deny access for guest dispatch. Similarly, an operator may manually stop a guest dispatch via a stopping mechanism (e.g., button) to override a permit or deny access signal if the operator finds any issues beyond those determined by the water attraction dispatch controller 114. The monitoring system 132 may also be used to recalibrate sensors on the water attraction 112.

The water attraction dispatch controller 114 may be in communication with multiple water attractions 112 within the water theme park 110. Further, individual attractions may share common features, such as a shared pool 124a that may be fluidically connected to not only the water slides 118a, 118b, 118c of the water attraction 112a, but also to the water of a lazy river water attraction 112b. As such, as provided herein, certain sensor 146 measurements may be applied to and considered as part of an attraction condition assessment for multiple portions of an individual water attraction 112 or even multiple water attractions 112. Accordingly, resolving attraction condition tasks for the shared pool 124a may also influence throughput in the lazy river water attraction 112b. For example, in the case of an out of tolerance water level condition (e.g., high water levels) in the shared pool 124a, the water attraction dispatch controller 114 may provide an instruction to a flotation device dispenser 125 to stop dispensing new flotation devices until the water level condition in the shared pool 124a is resolved. In another example, to resolve temperature and/or pH water condition levels in the lazy river water attraction 112b, pumping and/or other systems may divert water between the shared pool 124a and the lazy river water attraction 112b. In contrast, other water attractions (e.g., water attraction 112c) may be set apart from or fluidically isolated from other water attractions 112, and the associated shared pool 124 (e.g., shared pool 124b) is connected only with the water slides 118 of the individual isolated water attraction. As such, the water condition information of the shared pool 124a does not affect dispatch intervals for the isolated attraction 112c.

Figure 2:
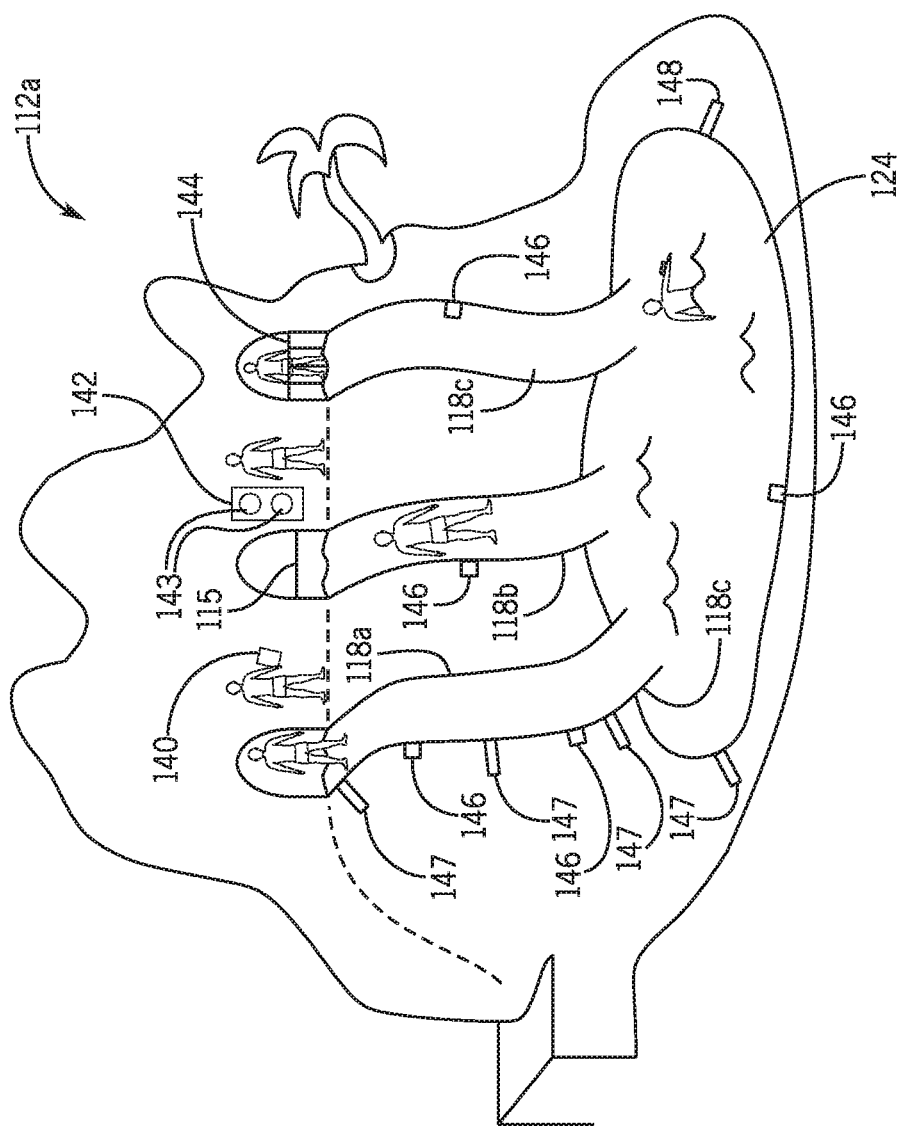
FIG. 2 is a schematic view of various dispatch devices of a water attraction utilizing a water attraction dispatch system in accordance with present techniques.

FIG. 2 illustrates a front perspective view of the water attraction 112a that may be used in conjunction with the water attraction dispatch controller 114 (FIG. 1) to provide instructions to control guest dispatch to one or more slides 118 based on an attraction condition determination by the water attraction dispatch controller 114. The depicted embodiment shows various examples of dispatch indicators that may be used alone or in combination with one another and on any suitable water attraction 112. In one embodiment, based on a determination from the water attraction dispatch controller 114 that the attraction condition and, in certain embodiments, the individual slide 118a condition is acceptable, a dispatch signal is provided to one or more visual indicator devices, such as a tablet 140 used by an operator, a light indicator 142 that may be viewed by an operator and/or guest, and/or an automated mechanical gate 144. The signal may be sent based on the conditions detected by water condition sensors 146 located throughout the water attraction 112a.

In one embodiment, the water condition sensors 146 may be located at various points of an individual slide 118 (e.g., slide 118c) of the water attraction 112a, such as at the dispatch location 116, in the middle of the slide 118, near the end of the slide 118, etc. In one embodiment, the sensor 146 may be a weight scale or weight sensor 146 mounted on a platform (e.g., the trap door 115) of the dispatch location 116. The presence of weight above a pre-determined threshold may indicate the presence of a guest to be dispatched. In another embodiment, if the attraction condition sensor 146 is a flow sensor or a water level sensor, sensed low water flow or water level by an individual attraction condition sensor 146 may trigger activation of one or more water injection points 147 closest to the attraction condition sensor 146 indicating the attraction condition data that is out of tolerance. In this manner, the water level for each individual slide 118 may be monitored and adjusted to maintain attraction conditions within pre-set tolerances. The water injection points 147 may also be coupled to the shared pool 124 to inject water and change the water level in the pool that receives the guests. Similarly, the water attraction 112a may also include one or more drain devices 148 that may also be triggered based on the attraction condition data. The attraction condition sensor 146 may detect conditions of the water source used for an individual slide 118 or for all of the slides 118 of the water attraction 112a. Moreover, the depicted attraction condition sensors 146 may refer to one or more attraction condition sensors 146 of one type or different types.

Additionally, other sensed data may be utilized by the water attraction dispatch controller 114, such as data read from radio frequency identification (RFID) tags incorporated into guest wearable devices (e.g., bracelets). The RFID tags may communicate with an electronic reader incorporated into an attraction condition sensor 146 to indicate presence of the tag. The RFID data may be utilized to indicate a presence of the guest in the queue, at the dispatch location 116, on the slide 118, and/or in the exit pool via one or more electronic readers on and/or near the slide 118. Moreover, the electronic reader and RFID tag communication may indicate the different speeds at which dispatched guests are traveling on the slide 118. For example, using data from a plurality of locations along the slide 118 may permit speed assessment.

The sensors 146 may include RFID or other wireless tags. In addition, such sensors 146 may also be associated with other ride components, such as inflatable devices, mats, or vehicles of the attraction 112. For example, the sensors 146 may be mounted to vehicles such that if the presence of the vehicle is detected (e.g., via RFID tag communication with one or more electronic readers located on the attraction 112), a subsequent guest or vehicle is not dispatched for a predetermined time period. The sensors 146 may also be configured to communicate on-board sensor data. For example, an inflatable vehicle, such as an inner tube or inflatable raft, may include an on-board pressure sensor that provides a signal to the dispatch controller 114, which in turn may monitor and send a dispatch signal based on whether the air pressure threshold in the inflatable vehicle is within tolerance (e.g., air pressure within a desired range). In addition, inflatable vehicles that are outside tolerance may be tagged for maintenance.

Additionally, the sensors 146 may include strain gauge sensors to indicate a presence of the guest on the slide 118. Each slide 118 may have a series of strain gauges along the slide 118 (e.g., embedded on or otherwise associated with the material forming the slide 118), creating a network (e.g., array) of strain gauges, that may be used to detect strain or change in resistance, such as by weight, force, and/or tension along the path. The deflection of the slide 118 caused by guests at various locations may be detected by the sensors 146 and mapped to various characteristic deflection profiles. For example a guest may cause a largest deflection at an individual sensor 146 closest to the guest. However, the deflection may propagate and be sensed by other sensors 146 in the array. Since strain values may vary based on guest weight, a profile of the entire slide 118 may be used to detect strain presence of the guest. A strain gauge algorithm may create a profile for the slide 118. The strain gauge sensors may detect strain within the strain gauge, which may be dynamically reported to the water attraction dispatch controller 114, which in turn assesses the data, e.g., with the strain gauge algorithm and relative to characteristic deflection profiles of the slide 118 to provide information about a presence and/or location of a guest on the slide 118 path. Knowledge of a guest location on the slide 118 and/or the guest's traveling speed may be used as additional sub-inputs to determine a dispatch interval or permission to dispatch by the water attraction dispatch controller 114. For example, the water attraction dispatch controller 114 may determine that an attraction condition is out of tolerance for a particular water attraction 112 based on the presence of a guest on the slide path as determined by the strain gauge algorithm based on strain map for the slide 118 path. Thus, guest dispatch may cease until the situation is resolved (i.e., the guest continues down the slide path to the shared pool 124a).

Figure 3:
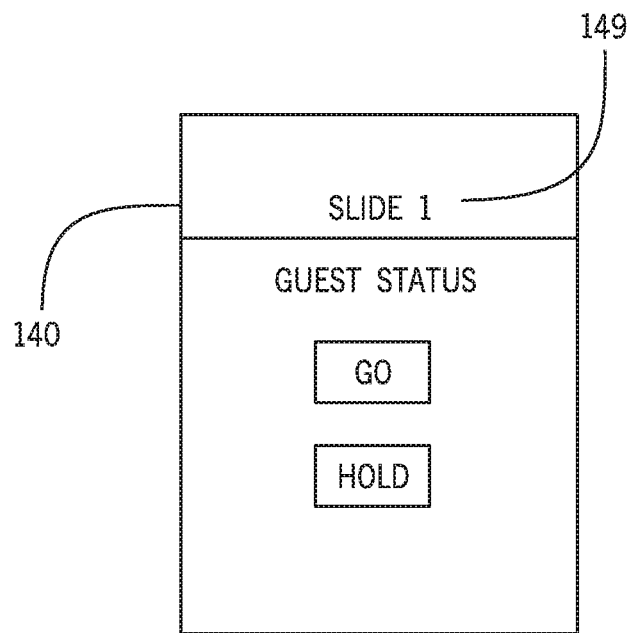
FIG. 3 is an example of a display including a permit dispatch indicator.

In one embodiment, the water attraction dispatch controller 114 may send a signal indicating permission or denial of guest dispatch, to a tablet 140 used by an operator. The tablet 140 may display a "GO" or "HOLD" prompt to indicate permission or denial of guest dispatch, as shown in FIG. 3. After receiving the "GO" signal on a tablet 140, e.g., as a switch from a previously-displayed "HOLD," the operator may dispatch the guest. The indication may be based on the signal sent by the water attraction dispatch controller 114, which may be based on current attraction conditions and/or additional inputs (e.g., presence of a guest on the ride or speed of current or past guest(s) on ride). As shown in FIG. 3, additional information may be relayed on the tablet 140, including, but not limited to, the slide identification information 149 (to prevent an operator inadvertently using the tablet 140 for another slide of the multi-slide water attraction 112a) of the water attraction 112, current interval dispatch time, a shared monitor screen with the monitoring system 132 to view attraction conditions, presence of a guest on a slide 118 path, etc. Thus, by viewing the attraction conditions in real time, the operator may be aware of the nature of any attraction condition issues.

Turning back to FIG. 2, the water attraction dispatch controller 114 may send a signal indicating permission or denial of guest dispatch to a light indicator 142 including one or more light sources display 143, e.g., a light emitting diode (LED). The light indicator 142 may include a red LED to indicate denial to dispatch, and a green LED to indicate permission to dispatch. The red or greed LED may illuminate based on a corresponding signal sent by the water attraction dispatch controller 114, based on current attraction conditions and/or additional inputs (e.g., presence of a guest on the ride or speed of current or past guest(s) on ride). The light indicator 142 may be viewed by an operator or a guest waiting to be dispatched. Thus, when the LED illuminates green, the guest may continue onto the water ride without waiting to be dispatched by an operator. Alternatively, an operator may dispatch the guest when the light indicator 142 illuminates green.

Moreover, although some of the following descriptions describe a deny dispatch signal and/or a red LED indicating the deny dispatch signal, which represents a particular embodiment, it should be noted that the methods and systems may be performed and implemented using any suitable arrangement of signals, such as the water attraction dispatch controller 114 dispatching based on only a permit dispatch signal (e.g., a fail-safe signal) without a denial to dispatch signal. That is, the default state of the attraction 112 may be a deny dispatch state. A permit dispatch signal is provided only based on data indicating attraction conditions that are associated with permitting dispatch. The attraction condition data is collected and assessed on an ongoing basis such that a permit dispatch signal is only valid for a predetermined number of dispatches and/or a predetermined amount of time. In one embodiment, the permit dispatch state is cleared after a single guest or single vehicle dispatch from the attraction 112. Once cleared, the attraction 112 returns to the default deny dispatch state until water attraction conditions associated with a permit dispatch signal are confirmed. Thus, in this embodiment the light indicator 142 may only include a green LED to indicate permission to dispatch based on the fail-safe permit dispatch signal sent by the water attraction dispatch controller 114. However, additional indicators or lights may also be present to indicate various operational features.

In yet another embodiment, the water attraction dispatch controller 114 may send a signal to automatically open or close a mechanical gate 144 to dispatch a guest. The signal may indicate an "open" or "close" signal to automatically open or close the mechanical gate 144. The mechanical gate 144 may open or close based on the corresponding signal sent by the water attraction dispatch controller 114, based on current attraction conditions and/or additional inputs (e.g., presence of a guest on the ride or speed of current or past guest(s) on the ride). Since the mechanical gate 144 may automatically open or close to dispatch a guest, there may be no need for an operator to dispatch guests. Thus, guests may continue onto the water ride themselves when the gate opens. However, an operator or a monitoring system may be used to monitor proper functionality of the mechanical gate 144. In an embodiment, the gate 144 may be operated under a default closed state associated with deny dispatch and may only open upon receipt of a permit dispatch signal to change to a permit dispatch state.

Figure 4:
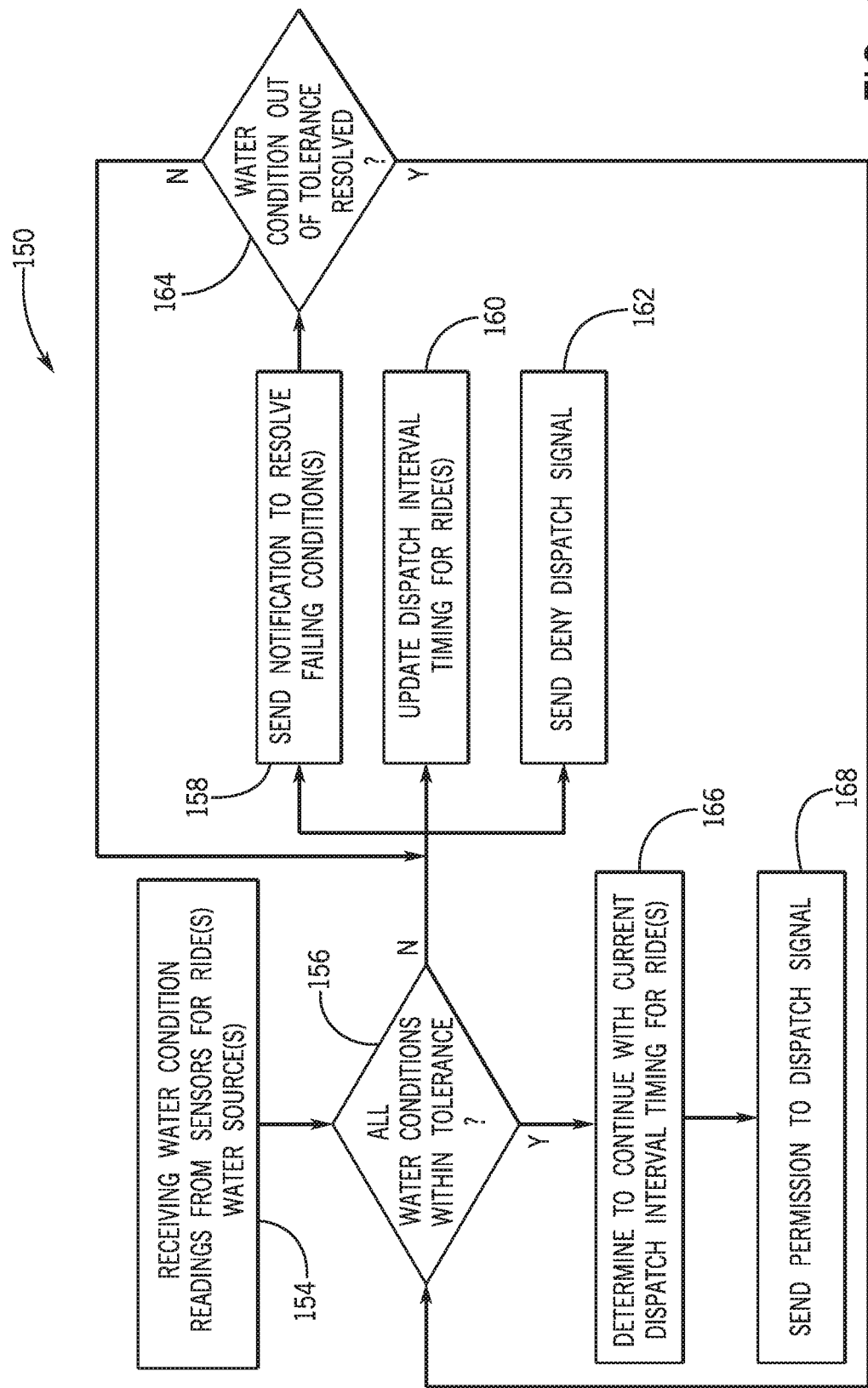
FIG. 4 is a process flow diagram of a water attraction dispatch system sending a permit or deny dispatch signal in accordance with present techniques.

To further illustrate the signal sent by the water dispatch controller 114 to permit or deny dispatch, FIG. 4 is a process flow diagram 150 of a dispatch signal determination technique. The process starts with the water attraction dispatch controller 114 receiving (block 154) attraction condition readings from the various attraction condition sensors 146 throughout the water attraction 112. The attraction condition readings or additional attraction condition data, such as the presence of a guest on the slide or the guest traveling speed, may also be acquired via the RFID tags, strain gauges, and wearables, as previously discussed.

Next, the water attraction dispatch controller 114 may determine whether (decision block 156) one or more attraction conditions are within a pre-determined tolerance. The water attraction dispatch controller 114 may calculate this determination by a machine algorithm. The algorithm may analyze the received data (e.g., attraction condition readings) and compare it to pre-determined tolerances that may be set by a user or operator. The machine algorithm may also calculate a pass or fail determination based on the tolerance calculation for an attraction condition, and then calculate an overall pass or fail determination based on all attraction condition tolerances. For example, the attraction condition data from the one or more sensors 146 may include different types of measurements, including water level data, pH levels, flow rate, chemical composition, etc. In one example, the sensors 146 may be a pH sensor that generates pH measurement data. The measurement data may be a pH value from a single location of the water attraction 112 or from multiple locations of the attraction. The measured pH value or values may be compared to a pre-set desired pH range. (e.g., about 7.2 to about 7.8). In another embodiment, the water level may be measured by optical sensors to determine if there is sufficient water fill in one or more areas of the water attraction 112. Depending on the nature of the measured attraction condition, values falling outside of the pre-set range or greater than or less than a pre-set threshold may be considered to be out of tolerance.

If one or more of the attraction conditions are not within its tolerance, then the water attraction dispatch controller 114 may send (block 158) an automatic notification to an operator to note the failing condition(s). Additionally or alternatively, upon determining that one or more attraction conditions are not within the pre-determined tolerance, the water attraction dispatch controller 114 may send a deny dispatch signal to a tablet 140 used by an operator, a display 143 used by an operator, and/or an automated mechanical gate 144 (FIG. 2). Further, the water attraction dispatch controller 114 may be configured to send the notification to the monitoring system 132. The monitoring system 132 may then send the notification to an assigned operator or park employee to resolve the out of tolerance attraction condition. The notification may indicate the particular attraction condition causing the overall attraction conditions to fail, and may indicate any related data, including but not limited to, attraction condition reading, a fault in the sensor 146 that may read the data, location of the attraction condition that is out of tolerance, steps to resolve the conditions that are out of tolerance, etc. In one embodiment, a single measured factor being out of tolerance may result in a deny dispatch signal being sent, regardless of the condition of the other measured factors. In other embodiments, the location of the out-of-tolerance factor may be considered. If the location is limited to a single slide 118 of a multi-slide attraction, the deny dispatch signal may only be sent to the dispatch location for the single slide while the other slides are unaffected.

Additionally, in certain embodiments, the dispatch interval time may be updated (block 160) from the current dispatch time to a new dispatch interval time based on the attraction condition not being within the tolerance and/or the attraction condition that is out of tolerance remaining in an unresolved state. After a notification to resolve the out of tolerance attraction condition has been assigned for resolution, the machine algorithm may check whether (decision block 164) the attraction condition has in fact been resolved. This check may be completed by another machine algorithm of the water attraction dispatch controller 114 that monitors and detects a change in sensor data for an attraction condition that was assigned for resolution. Alternatively, an operator or monitoring system 132 may mark the assigned task as completed. Thus, this part of the machine algorithm may be dependent on the out of tolerance attraction condition detected in the previous steps. If the machine algorithm determines the resolution did not result in the attraction condition to be within tolerance, then the process 150 may return to sending (block 158) notification to resolve, update (block 160) dispatch interval timing, and send (block 162) deny dispatch signal, as previously discussed.

However, if a resolution results in the attraction condition to be within tolerance or if the initial attraction condition readings were within the tolerance, then the process 150 may determine (block 166) to continue with the current dispatch interval timing for the water attraction ride(s) 112. Accordingly, the water attraction dispatch controller 114 may send (block 168) a permission to dispatch signal to a tablet 140 used by an operator, a display 143 used by an operator, and/or an automated mechanical gate 144, as discussed in FIG. 2. There may be various attraction condition factors monitored and considered by the process 150 when sending a permission or deny dispatch signal.

Figure 5:
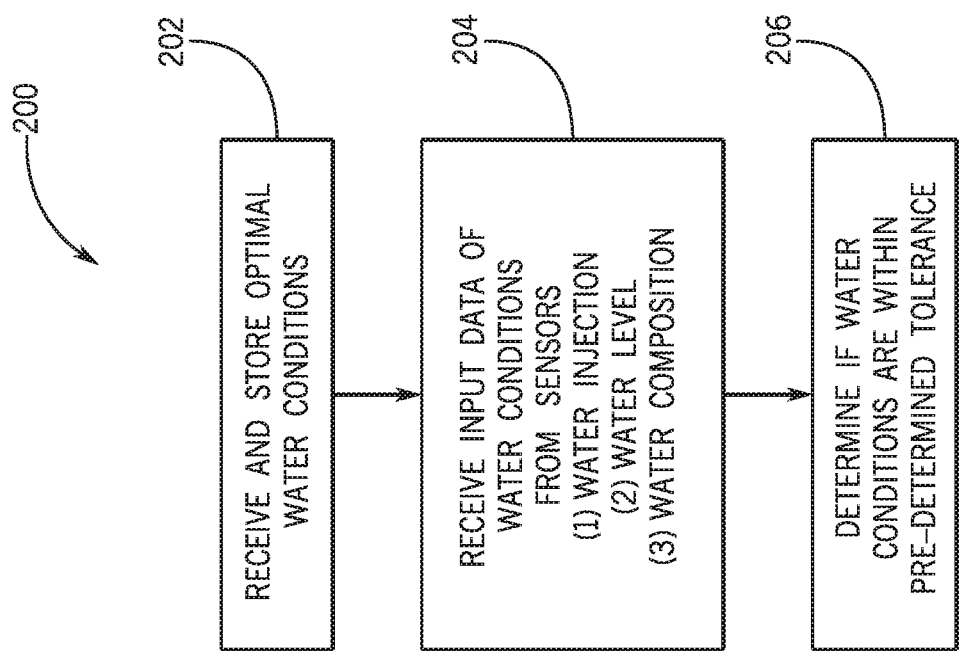
FIG. 5 is a process flow diagram of a technique for assessing dispatch conditions in accordance with present techniques.

As illustrated by the process 200 of FIG. 5, the water attraction dispatch controller 114 considers various attraction condition factors or inputs for dispatching guests. The process may begin with the water attraction dispatch controller 114 receiving (block 202) optimal attraction condition instructions from a user design, which may be stored in the memory of the water attraction dispatch controller 114. The optimal attraction condition instructions may include predetermined tolerances for each attraction condition considered. As previously discussed, a processor-based machine algorithm of the water attraction dispatch controller 114 may calculate whether an attraction condition is out of tolerance.

Once the water attraction dispatch controller 114 has received and stored the optimal or desired attraction conditions, it may receive (block 204) sensor data input for multiple attraction conditions. The attraction conditions may include, but are not limited to, water injection, water level, water composition, guest status on or near the water attraction, misbehaving guest on or near the water attraction (e.g., guest blocking or staying inside slide 118 path), and environmental changes (e.g., weather changes) on or near the water attraction. Each individual attraction condition may be associated with respective individual tolerance or states to pass or to be part of a permit dispatch status. Certain attraction conditions may be binary. For example, an attraction condition may be "guest at dispatch location?" with "yes" being associated with a permit dispatch status while "no" is associated with a fail and a resulting deny dispatch status. In another example, a water pH level within a desired range is associated with a permit dispatch status while a pH outside the range is associated with a deny dispatch status. As provided herein, the deny dispatch status is triggered when only one or at least one of a plurality of attraction conditions is outside of tolerance or fails. Conversely, the permit dispatch status is associated with all or most conditions being within tolerance or passing. As provided herein, a water attraction 112 may have a default deny dispatch status as a fail-safe.

In one embodiment, proper water injection may be an attraction condition considered by the water attraction dispatch controller 114 when determining guest dispatch. Water injection points 147 on a water slide 118 of the water attraction 112 may influence the water flow rate on the water slide 118. Constant flow of water may allow a guest to continue down the water slide 118 without stopping or becoming cold. Thus, there may be one or more injection points throughout the water slide 118 of the water attraction 112. The tolerance for the water injection condition may be set to allow a constant flow of water detected throughout the slide 118. Therefore, the tolerance may also be set to have sensors 146 detect water at different points on the slide 118.

In another embodiment, proper water level may be an attraction condition considered by the water attraction dispatch controller 114 when determining guest dispatch. Water level throughout the water attraction 112 may be considered since it ensures proper flow rate throughout the water attraction 112. The sensors 146 may detect water levels for various parts of the water attraction 112, which may include water levels on slides 118, the water pool 124 for the one or more slides of a water attraction 112, and/or the water source for a water attraction 112. The threshold or tolerance for the water level may be set to allow a constant flow of water for the different parts of the water attraction 112, as previously mentioned.

In yet another embodiment, proper water composition may be an attraction condition considered by the water attraction dispatch controller 114 when determining guest dispatch. Water composition may be considered to ensure chemical balance of the water, which may further ensure minimization of water contamination. The sensors 146 may detect pH level for various parts of the water attraction 112, which may include pH levels of water on the slide(s) 118, the water pool 124 for the one or more slides 118 of the water attraction 112, and/or the water source for the water attraction 112. Maintaining proper water composition, such as by the pH level and/or chlorine levels, may prevent guest discomfort upon water contact, maintain equipment, and maintain chlorine functionality to prevent contamination. The tolerance for the pH level may be set at 7.2 to 7.8. Another sub-factor that may be used as an indicator for proper water composition may include, but is not limited to, the presence or absence of specific contaminants. The threshold may be set according to a tolerable level of the type and amount of contamination.

In another embodiment, a proper dispatch interval may be considered by the water attraction dispatch controller 114 when determining whether to deny or permit guest dispatch. The dispatch interval may be considered to ensure an efficient guest riding rate and to prevent having multiple riders on the same slide without maintaining an appropriate interval time between their dispatches. The tolerance level set for dispatch interval time may be set to the average time it takes for a guest to reach the bottom of the slide or water pool 124 after dispatch. The tolerance may additionally include a buffer time to prevent multiple guest dispatches in close proximity to each other. Other sub-factors that may be considered when a dispatch interval tolerance is set may be the number of slides 118 for the water attraction 112 that may feed into the water pool 124, the length of the slide 118 and/or overall water attraction 112, etc.

After receiving input data for the various attraction conditions, including water injection, water level, water composition, and dispatch interval, the processor-based machine algorithm of the water attraction dispatch controller 114 may determine (block 206) whether an attraction condition is out of tolerance. The machine algorithm may implement the determination by comparing the received input data to the pre-set tolerances set by a user. Thus, the water attraction dispatch controller 114 may monitor and determine whether attraction conditions are within pre-set tolerances to allow permission to dispatch a guest for a water attraction 112.

Figure 6:
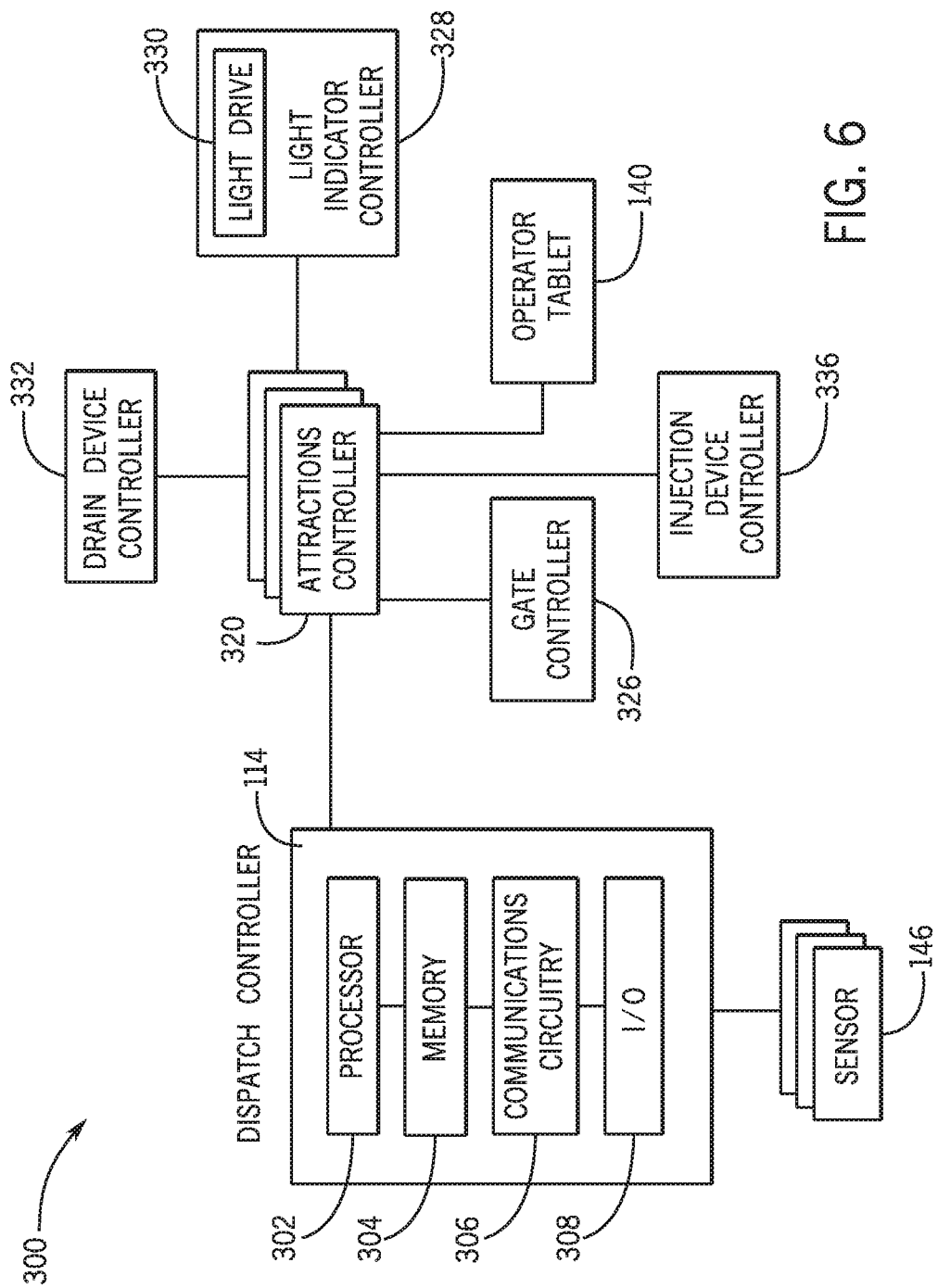
FIG. 6 is a block diagram of a water attraction dispatch system in accordance with present techniques.

FIG. 6 is a block diagram of a water attraction dispatch system 300. The system 300 includes the water attraction dispatch controller 114, which may include a memory 304 storing instructions executable by a processor 302 to perform the methods and control actions described herein. The processor 302 may include one or more processing devices, and the memory 304 may include one or more tangible, non-transitory, machine-readable media. By way of example, such machine-readable media can include RAM, ROM, EPROM, EEPROM, or optical disk storage, magnetic disk storage or other magnetic storage devices, or any other medium which can be used to carry or store desired program code in the form of machine-executable instructions or data structures and which can be accessed by the processor 302 or by other processor-based devices (e.g., mobile devices). For example, the water attraction dispatch controller 114 may be accessed by an operator interface (e.g., a computer-based workstation or a mobile device, and/or may include an input/output interface 308 and a display). The water attraction dispatch controller 114 may include communications circuitry 306, such as antennas, radio transceiver circuits, signal processing hardware and/or software (e.g., hardware or software filters, A/D converters, multiplexer amplifiers), or a combination thereof. The communications circuitry 306 may be configured to communicate over wired or wireless communication paths via IR wireless communication, satellite communication, broadcast radio, microwave radio, Bluetooth, Zigbee, Wifi, UHF, NFC, etc. Such communication may also include intermediate communications devices, such as radio towers, cell towers, etc. While the processor 302, memory 304, communications circuitry 306, and operator interface elements such as the input/output interface have been discussed in the context of the water attraction dispatch controller 114, it should be understood that at least some of these hardware components may also be present in other controllers of the system 300.

The water attraction dispatch controller 114 is in communication with an attraction controller 320 to provide a signal indicative of a dispatch status. Based on data generated by one or more sensors 146, the dispatch controller may assess the attraction condition to generate the dispatch status signal. The one or more sensors 146 may include water level sensors, flow rate sensors, pH sensors, temperature sensors, and/or chemical composition sensors (e.g., oxidative reduction potential sensors indicative of chlorine sterilization activity, free chlorine sensors, combined chlorine sensors) by way of example. In addition, the one or more sensors 146 may include optical sensors that detect passage of a guest or wireless sensors (e.g., RFID, NFC) that communicate with guest-worn devices to register guest location within the water attraction 112 (see FIG. 1).

The attraction controller 320 may use the dispatch status together with the guest location, determined via operator assessment or from sensor data, to control dispatch. For example, each attraction may have a pre-set or desired dispatch interval (e.g., every 30 seconds) for guest dispatch. Immediately after guest dispatch, the attraction controller 320 may cause any associated dispatch indicators (e.g., the guest tablet 140, the light indicator 142) or gate controllers 326 to be in deny dispatch mode until the dispatch interval has elapsed, regardless of the attraction condition indicated by the dispatch status signal. In this manner, no additional guests are permitted to dispatch (e.g., enter a slide) until sufficient time has elapsed to allow the previous guest to complete the attraction run and exit. This time may be estimated for a range of guest sizes and weights to determine the appropriate dispatch interval. After the dispatch interval has elapsed from the time of dispatch of the previous guest, the attraction controller 320 resolves the dispatch status signal from the water attraction dispatch controller 114. If the dispatch status signal is indicative of acceptable attraction conditions, the dispatch indicators or gate controllers 326 may enter a permit dispatch mode to permit the next guest to be dispatched. If the dispatch status signal is indicative of unacceptable attraction conditions, the dispatch indicators or gate controllers 326 may enter a deny dispatch mode to prevent the next guest from being dispatched. For example, based on the dispatch status signal, a light drive 330 of a light indicator controller 328 may be driven to light a green or red light (e.g., light sources 143) and/or a signal may be sent to the operator tablet 140 indicating a GO or HOLD. The gate controller 326 may cause the gate (e.g., gate 144) to move between the up and down configuration.

In addition to facilitating guest dispatch, the system 300 may also operate to automatically resolve certain attraction condition tasks. For example, based on the sensor data, the attraction controller 320 may cause a drain device controller 332 or an injection device controller 336 to be activated to change attraction conditions to achieve measurements that are within tolerance.

While only certain features of the present disclosure have been illustrated and described herein, many modifications and changes will occur to those skilled in the art. It is, therefore, to be understood that the appended claims are intended to cover all such modifications and changes as fall within the true spirit of the disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A water attraction dispatch system, comprising:
a water attraction;
a plurality of sensors of the water attraction; and
a dispatch controller comprising a processor and a memory, wherein the memory stores instructions executable by the processor, the instructions configured to cause the dispatch controller to:
receive attraction condition data from the plurality of sensors of the water attraction, wherein a portion of the plurality of sensors comprises a network of strain gauge sensors along a slide path of an individual slide of the water attraction;
determine guest position data on the individual slide based on the network of strain gauge sensors and a strain map of the individual slide, wherein the strain map corresponds to a profile of the individual slide associated with the guest position data;
determine a dispatch status of the individual slide of the water attraction based on the attraction condition data and the guest position data, wherein the determined dispatch status comprises a permit dispatch status or a deny dispatch status; and
transmit a signal indicative of the dispatch status to a controller of the water attraction.

2. The system of claim 1, wherein the received attraction condition data comprises water level data, water flow data, water composition data, water pH data, environmental changes, weather changes, or a combination thereof.

3. The system of claim 1, wherein the received attraction condition data comprises guest status data, guest position data, or a combination thereof.

4. The system of claim 1, wherein the network of strain gauge sensors is configured to measure guest-associated deflection propagated along the network, wherein the guest-associated deflection is compared to a plurality of characteristic deflection profiles of the strain map to determine guest location on the individual slide.

5. The system of claim 1, wherein a default state of the water attraction is the deny dispatch status.

6. The system of claim 1, wherein the stored instructions are configured to cause the dispatch controller to determine or maintain the deny dispatch status based on the attraction condition data from only one sensor of the plurality of sensors being out of tolerance.

7. The system of claim 6, wherein the received attraction condition data is out of tolerance based on a measured data value of the attraction condition data being outside of a predetermined range, above a pre-determined threshold, or below the pre-determined threshold.

8. The system of claim 7, wherein the received attraction condition data is out of tolerance when a measured water pH is outside of a range of about 7.2 to about 7.8.

9. The system of claim 7, wherein the received attraction condition data is out of tolerance when a measured water level in the attraction is lower than a pre-determined level.

10. The system of claim 1, comprising a gate controller located at a dispatch location of the water attraction, wherein the determined dispatch status comprising the deny dispatch status causes the gate controller to close a gate or keep the gate closed.

11. The system of claim 1, comprising a light indicator located at a dispatch location of the water attraction, wherein the determined dispatch status comprising the permit dispatch status causes the light indicator to drive a light source.

12. The system of claim 1, wherein the determined dispatch status comprises a first dispatch status of an individual slide of a multi-side attraction, the first dispatch status comprising the deny dispatch status based on the received attraction condition data of an individual sensor of the plurality of sensors, the individual sensor associated with the individual slide and a second dispatch status of other slides of the multi-side attraction, wherein the second dispatch status comprises the permit dispatch status.

13. The system of claim 1, wherein the determined dispatch status comprises an overall dispatch status for slides of a multi-slide attraction, the overall dispatch status comprising the deny dispatch status based on the received attraction condition data of an individual sensor of the plurality of sensors, wherein the individual sensor is associated with a shared water source for the slides of the multi-slide attraction.

14. A water attraction dispatch system, comprising: a water attraction; a plurality of sensors of the water attraction; and a dispatch controller comprising a processor and a memory, wherein the memory stores instructions executable by the processor, the instructions configured to cause the dispatch controller to: receive attraction condition data from the plurality of sensors of the water attraction; determine a deny dispatch status for an individual slide of a plurality of slides of the water attraction based on attraction condition data associated with the individual slide; determine a permit dispatch status for other slides of the plurality of slides of the water attraction based on attraction condition data associated with the other slides and attraction condition data of a shared water resource; and transmit a signal indicative of the deny dispatch status and the permit dispatch status to a controller of the water attraction; wherein the plurality of sensors comprises a network of strain gauge sensors along a slide path of the individual slide; and wherein the network of strain gauge sensors and a strain map corresponding to the individual slide associated with a measured guest-associated deflection by the network of strain gauge sensors are used to determine a guest position.

15. The system of claim 14, wherein the measured guest-associated deflection is used in conjunction with a guest traveling speed to determine the permit dispatch status or the deny dispatch status.

* * * * *

UNITED STATES PATENT AND TRADEMARK OFFICE
CERTIFICATE OF CORRECTION

PATENT NO. : 10,589,182 B2
APPLICATION NO. : 16/107325
DATED : March 17, 2020
INVENTOR(S) : Nathaniel David Helmick, IV, Elliot Taylor and Justin Michael Schwartz It is certified that error appears in the above-identified patent and that said Letters Patent is hereby corrected as shown below:

On the Title Page

Item (12), should read:
--Helmick IV et al.--

Item (72) Inventors, should read:
--(72) Inventors: Nathaniel David Helmick IV, Winter Park, FL (US);
 Elliot Taylor, Winter Springs, FL (US);
 Justin Michael Schwartz, Orlando, FL (US)--

Signed and Sealed this
Nineteenth Day of March, 2024

Katherine Kelly Vidal
*Director of the United States Patent and Trademark Office*